United States Patent [19]

Szasz et al.

[11] 4,358,855

[45] Nov. 9, 1982

[54] X-RAY PHOTOGRAPHING AND DEVELOPING APPARATUS

[75] Inventors: Károly Szász; Sándor Meszáros, both of Budapest, Hungary

[73] Assignee: Medicor Muvek, Budapest, Hungary

[21] Appl. No.: 175,436

[22] Filed: Aug. 6, 1980

[51] Int. Cl.³ .............................................. G03B 41/16
[52] U.S. Cl. ..................................... 378/99; 358/111; 378/173
[58] Field of Search ............... 250/402, 416 TV, 470; 358/111, 130

[56] References Cited

U.S. PATENT DOCUMENTS 3,924,064  12/1975  Nomura ........................ 250/416 TV
4,276,478   6/1981  Meszaros ............................ 250/470

Primary Examiner—Craig E. Church
Attorney, Agent, or Firm—Karl F. Ross

[57] ABSTRACT

An X-ray system for patient diagnostic services in which the patients are X-rayed at several locations and picture amplifiers pick up the X-ray images and are associated with television cameras which transmit video signals both to a monitor at the X-ray location and to a video signal distributor which delivers signals from a selected camera to a central photographing unit. This unit has a further video monitor, an optical system and shutter and means for replaceably positioning films in the focal plane of these opticals. The exposed film is continuously developed.

4 Claims, 1 Drawing Figure

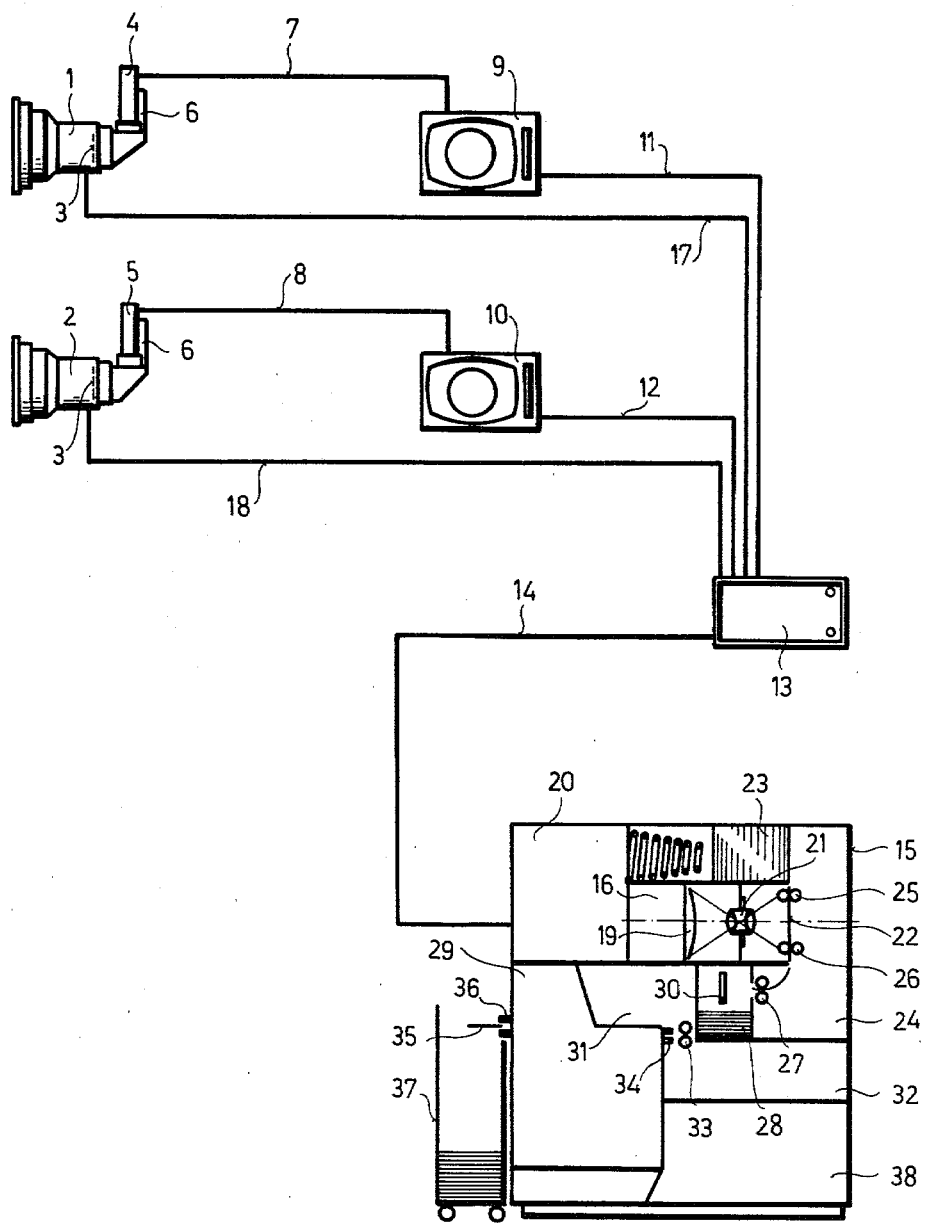

X-RAY PHOTOGRAPHING AND DEVELOPING APPARATUS

FIELD OF THE INVENTION

The present invention relates to an X-ray photographing and developing apparatus for servicing a workplace adapted to make roentgenograms, the workplace being equipped with a picture amplifier, a television recording camera coupled thereto and a workplace monitor connected to the video output of the camera.

BACKGROUND OF THE INVENTION

It is well-known that X-ray photographing equipment should be operated in such manner, that during the time period of exposure an unexposed film is fixed in a plane corresponding to the area from which the picture is to be taken, and the equipment should provide for a fresh film supply.

A common feature of much earlier equipment is that the exposure and the changing of the films occur in each case at the corresponding X-ray workplace. In other X-ray equipment a so-called magazine store, adapted to store a plurality of unexposed and exposed films, is built together with a developing apparatus.

The film producing technique carried out at individual workplaces increases the demand on space and material.

In the photographing systems equipped with a picture amplifier (image intensifier), the role of the picture amplifier lies in the correct determination of the area of exposure and in obtaining preliminary picture information. The actual exposure, in the earlier systems, is not taken through the picture amplifier, but it is taken by the exposure of an unexposed film arranged across the path of the X-ray beams. It is well-known in the art that substantially higher radiation intensity is required for taking an exposure that to the monitoring of a picture through the picture amplifier. In such photographing systems the X-ray specialist does not have the possibility of checking the picture through a monitor during the exposure and, for that reason, frequently more exposures are taken than it is required.

According to another conventional photographing method the image obtained on the screen of the picture amplifier is transferred through a suitable optical light splitting device first to a television recording camera and second to a special photographing unit (spot-exposure technique). The light intensity of the picture on the screen of the picture amplifier is generally not sufficient to enable the preparation of pictures of acceptable quality with practical film sensity values. Therefore when exposures are taken the radiation intensity is increased in a pulse-like manner and the light splitter is adjusted in such a way that the television recording camera should receive about 3 per cent of the full output of the picture amplifier. In such systems picture size reduction is carried out by the optical system used for taking the exposure in order to increase thereby the illumination of the film. The quality of the so-prepared reduced scale exposures does not reach the quality of full scale exposures taken by direct exposure, and this quality is not sufficiently high for forming an accurate medical diagnosis.

OBJECT OF THE INVENTION

The object of the invention is to provide an X-ray photographing and developing apparatus that renders film preparation at each workplace unnecessary, that substantially reduces the radiation load of the patient during exposure and which provides at least as high picture quality as can be attained by exposures taken directly by the X-ray beams.

SUMMARY OF THE INVENTION

The invention is based on the discovery that the picture being displayed on the screen of the picture amplifier, which has sufficiently good quality, can be converted by means of television scanning and picture reconstruction techniques into a high quality television picture from which a normal photographical exposure can be taken. The application of the television technique renders unnecessary the use of high X-ray doses during the exposure and allows film preparation centrally, far away from the respective workplaces.

According to the invention an X-ray photographing and developing apparatus has been provided for servicing workplaces, in which each workplace comprises a picture amplifier, a television recording camera coupled thereto, and a workplace monitor coupled to the output of the camera. The apparatus comprises several workplaces and a central video distributor, which receives the video cables of the recording cameras associated with the respective work places, the output of the video distributor is coupled through a cable to a second monitor arranged in a central photographing unit, and before the screen of the second monitor an optics and shutter assembly is arranged having an image plane in which an unexposed film is located in a planar guided arrangement. The central photographing unit is coupled through cables signalling its state of engagement and the parameters representing the exposure to the respective workplaces, and in the central photographing unit there is provided a storage place for the unexposed films and a further storage place for the exposed films, and a film changing device comprising pairs of rollers is arranged between the storage places and the storage place for the exposed films is coupled through a planar film changing device with transport rollers to an automatic developing apparatus.

The X-ray photographing and developing apparatus according to the invention enables the common servicing of several workplaces, whereby the equipment used in the individual workplaces will be substantially less complicated. There is no need to use increased X-ray doses for taking high quality pictures and the pulse-like mode of operation of the X-ray tube will also be eliminated. The X-ray specialist can furthermore continuously monitor the picture on the screen of the workplace monitor and he can start the exposure at the most appropriate moments.

BRIEF DESCRIPTION OF THE DRAWING

The invention will now be described in connection with a preferred embodiment thereof, reference being made to the accompanying drawing, the sole FIGURE of which is a block diagram.

SPECIFIC DESCRIPTION

The apparatus comprises workplace units arranged at the sites where the X-ray pictures are taken, and a central unit. In the drawing, units associated with two work places are shown, the number of work places can, however, be increased without limitation to meet user requirements.

In each workplace, opposite the patient to be examined in the path of the emitted X-ray beams, picture amplifier 1 or 2 is arranged, which is built together with a television camera 4 or 5 so that the camera provides a video signal from the optical picture visible on screen 3 of the picture amplifier 1 and 2 by means of standard television scanning technique.

Outputs of recording cameras 4 and 5 are coupled through video cables 7 and 8 to respective workplace monitors 9 and 10 located at the associated work places. The video signals are coupled additionally through video cables 11 and 12 to video distributor 13 belonging to the central unit.

For identifying the data of patients a patient identification projection assembly 6 is built together with the respective recording cameras 4 and 5. The patient inserts his card comprising his name and his identifying data at the beginning of the examination into the assembly 6 and it projects the data from the card into a predetermined field of the television camera 4 and 5.

The output of the video distributor 13 is coupled through cable 14 to central photographing unit 15 comprising a second monitor 16. The central photographing unit 15 can service only one of the working places at a time, and during the servicing operation the possibility of taking pictures from the other working places is blocked. The cooperation between the working places is provided through appropriate enabling and inhibiting circuits. The workplace units receive information relating to the engagement of the central photographing unit 15 through cables 17 and 18 from the central video distributor 13.

In the central photographing unit 15 on the viewing screen 19 of the second monitor 16 there will be visible the image obtained by television scanning from the screen 3 of the picture amplifier associated with the selected working place. In front of the viewing screen 19 a lens/shutter assembly 21 is placed in the closed space, and the assembly 21 provides the image of the picture on the viewing screen 19 on a film 22 arranged behind the assembly 21 in such a way that the between the lens shutter provides an exposure exactly for the duration of a complete television picture.

A closed film storage space 23 is arranged in the central photographing unit 15 in which a predetermined number of unexposed films can be stored. From the storage space 23 the next film is taken out by means of appropriate movements of two pairs of rollers 25 and 26 forming part of a film changing assembly located in space 24. The film 22 is stretched between the roller pairs 25 and 26 in the plane of exposure. The film changing assembly in the space 24 provides for the transportation of the exposed film 22 into storage place 28 for exposed films. The movement of unexposed and exposed films occurs simultaneously with unidirectional translation steps. A pair of rollers 27 is placed in front of the inlet opening of the storage place 28 which is moved together with the movement of roller pairs 25 and 26. The quantity of exposed films stored in the storage place 28 is sensed by sensor switch 30, which provides a signal when the number of the stored exposed films exceeds a predetermined maximum allowed value.

From the storage place 28 the exposed films are moved through transport rollers 33 into inlet opening 34 of an automatic developing apparatus 29. The movement of the film is controlled by a planar film changing assembly arranged in room 32 extending between storage place 28 and the automatic developing apparatus 29.

The movement of the exposed films is comparatively slow (with a speed of between about 100 and 120 centimeters per minute), but this movement of the exposed films is continuous which is in contrast to the quick but stepwise movement of the unexposed films. This way the storage place 28 performs the task of a buffer store, too. The sensor switch 30 when being operated controls an electronic control unit arranged in room 31 to block the movement of unexposed films and thereby the work of taking exposures. The blocking period lasts generally for ten minutes, and during this period of time about 85–90 films are developed. After the operational pause the storage place 28 will be ready to receive a corresponding number of recently exposed films.

From the automatic developing apparatus 29 the developed films 35 move through outlet opening 36 to collector carriage 37 that can be rolled beside the central photographing unit 15. In order to economize the developing process a silver regenerating apparatus is arranged in space 38 of the unit.

The operation of the central X-ray photographing and developing apparatus is as follows.

In each working place the doctor adjusts the X-ray apparatus by watching the screen of the associated work place monitor according to diagnostic exposure requirements as is known in conventional picture amplifier techniques. When he intends to take an exposure he has to report this intention to the central photographing unit, which in response to such a request controls the video distributor 13 so that this particular working place will be coupled to the central photographing unit 15. The central photographing unit 15 will carry out the exposure with parameters (dosage, length of exposure series, etc.) determined and adjusted at the particular work place, and the second monitor 16 will display the picture of the concerned work place monitor 9. The time and sequence of openings of the lens-shutter assembly 21 depends on the adjusted parameters of the exposure series. The film changing apparatus located in room 24 provides for the supply of respective fresh unexposed films in the plane of exposure during each exposure. Naturally, conventionally designed known control electronics sees to the fact that only such exposure parameters can be adjusted, which can be realised within the range of limitations of the apparatus.

The main difference compared to conventional photographing methods lies in that there will be no need for taking a picture from the image displayed on the screen 3 of the picture amplifier through a light splitter with the small light intensity available there, but a good quality picture can be taken from the screen 19 of the second monitor 16 with a much higher light intensity chosen in accordance with the possibilities of electronic imaging technique. By using this photographing method the X-ray load of the patient will be substantially reduced, because the exposure dosage should be chosed to such an extent only that is required for providing an image on the screen of the picture amplifier so that is should be sufficient for obtaining an electronically scanned picture of required quality.

The substantial decrease of radiation intensity provides for the application of small-size X-ray focuses enabling a higher resolution and an increased contrast gradation.

Since the doctor sees on the screen of his work place monitor 9 the picture from which the photograph is taken, he can choose and check the optimum time and positioning of the exposure.

The patient identification projecting assembly 6 arranged at each work place provides for the good identification of the roentgenograms by projecting the identification data and the serial number of the exposure in the imaged picture.

The provision of the central photographing unit 15 is motivated among other things by the fact that the photographs are taken discontinuously at the individual workplaces, and between respective intervals at a given workplace there is the possibility of servicing other workplaces. In order to provide for undisturbed continuous working conditions, it is preferable to use more than one central photographing unit 15 in roentgen departments having several such workplaces, by which more than one workplace can operate simultaneously.

The speciality of roentgenological work makes it necessary that certain workplaces should obtain at least in given periods unconditional priority i.e. they must not wait in case of need for an exposure. With appropriate design of the central control unit it can be assured that each workplace of higher priority will have an access to the central photographing unit 15 when such demand arises, even if the work of another workplace should therefore be interrupted.

The above described design of the central photographing unit 15 renders the application of photographing equipment used heretofor at each workplace to be unnecessary, which is connected with substantial savings in costs.

According to our experience the photographing of the second monitor 16 can provide pictures having such a good quality, in which the resolution is determined by the smallest focal size that can be realized by the X-ray equipment. If this minimum focal size is e.g. between 0.2 and 0.3 mm, the resolution of the picture obtained through the picture amplifier and the television monitor will have a corresponding value, if the number of lines is chosed sufficiently high e.g. to 1240 lines/pictures in the video system. This resolution coincides with the resolution ability of an average human eye. It should be noted that the resolution of the screen of the picture amplifier alone is much more favorable than the above value, so that the application of the picture amplifier does not decrease the quality of the obtained pictures.

We claim:

1. An X-ray system for medical diagnostic purposes, comprising:

a plurality of patient X-ray locations, each of said locations being provided with:

a picture amplifier disposed in the path of an X-ray beam adapted to pass through a patient;

a transmission camera operatively connected to said picture amplifier for generating a video signal representing a roentgenographic image of the patient, and a video monitor connected to said camera for displaying a television image corresponding to said roentgenographic image;

a video distributor operatively connected to all of said cameras for selectively delivering the video signals from said cameras to an output of said distributors; and a central photographing unit including:

a further video monitor connected to said output of said distributor for displaying a video image corresponding to the roentgenographic image of a selected camera, a film supply and means for advancing unexposed photographic films in a focal plane spaced from said further video monitor and for advancing exposed photographic film from said plane to a storage space for the exposed film, developing means continuously withdrawing exposed film from said space and chemically processing said exposed film to develop photographic images representing the successive video images of said further monitor and the corresponding roentgenographic images of said patients, and an optical lens system including a shutter between said further monitor and said plane for exposing film in said plane to the video image of said further video monitor so as to form latent photographic images on said film.

2. The X-ray system defined in claim 1 wherein said central developing unit includes a film changing device operable for stepwise film movement, said space being provided with a sensing switch responsive to the number of exposed films stored in said space and adapted to block further operation of said film changing device when said number reaches a predetermined maximum.

3. The X-ray system defined in claim 1 or claim 2 wherein each of said cameras is provided with means for transmitting a video image of data carried by a card inserted into said cameras by the respective patient.

4. The X-ray system defined in claim 1 or claim 2 wherein said central developing unit includes a silver recovery apparatus.

* * * * *